United States Patent
Ye et al.

(10) Patent No.: US 7,381,985 B1
(45) Date of Patent: Jun. 3, 2008

(54) BIS-CARBAZOLE MONOMERS AND POLYMERS

(75) Inventors: Qing Ye, Schenectady, NY (US); Jie Liu, Niskayuna, NY (US); James Anthony Cella, Clifton Park, NY (US); Kyle Erik Litz, Ballston Spa, NY (US); Joseph John Shiang, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/610,032

(22) Filed: Dec. 13, 2006

(51) Int. Cl.
*H01L 29/08* (2006.01)
*H01L 35/24* (2006.01)
*H01L 51/00* (2006.01)

(52) U.S. Cl. ..................................... 257/40
(58) Field of Classification Search ................ 257/40
See application file for complete search history.

(56) References Cited

U.S. PATENT DOCUMENTS

| | | | |
|---|---|---|---|
| 2003/0027016 A1* | 2/2003 | Ara et al. | 428/690 |
| 2005/0116622 A1 | 6/2005 | Lo et al. | |
| 2005/0118430 A1* | 6/2005 | Doi et al. | 428/413 |
| 2006/0003183 A1 | 1/2006 | Helber et al. | |
| 2006/0073357 A1* | 4/2006 | Brunner et al. | 428/690 |

FOREIGN PATENT DOCUMENTS

| JP | 63-013048 | * | 1/1988 |
|---|---|---|---|
| JP | 08-003547 | * | 1/1996 |
| WO | WO 2004072205 A2 | * | 8/2004 |

OTHER PUBLICATIONS

Wang et al., Synthesis and Characterization of Poly(N-arylcarbazole-alt-aniline) Copolymers as Blue-Emitting Host Matrix for Polymer Light-Emitting Diodes, Mol. Cryst. Liq. Cryst., vol. 459, pp. 95/[375]-107/[387], 2006.*

(Continued)

*Primary Examiner*—Jerome Jackson
*Assistant Examiner*—Anthony Ho
(74) *Attorney, Agent, or Firm*—Mary Louise Gioeni; William E. Powell, III

(57) ABSTRACT

The invention relates to compounds of formula I

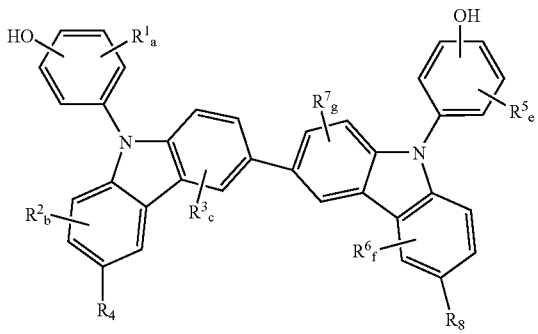

Formula I wherein
$R^1$, $R^2$, and $R^4$ are independently at each occurrence a $C_1$-$C_{20}$ aliphatic radical, a $C_3$-$C_{20}$ aromatic radical, or a $C_3$-$C_{20}$ cycloaliphatic radical; $R^3$ and $R^5$ are independently at each occurrence hydrogen, a $C_1$-$C_{20}$ aliphatic radical, a $C_3$-$C_{20}$ aromatic radical, or a $C_3$-$C_{20}$ cycloaliphatic radical; and
a, b and d are independently 0 or an integer ranging from 1 to 3.

The invention further relates to polymers derived from compounds of formula I. The polymers may be polyesters, polyethers, polycarbonates, polyestercarbonates, polyetherketones, or polyethersulfones. Compounds and polymers of the invention find use in light emitting devices.

27 Claims, 3 Drawing Sheets

OTHER PUBLICATIONS

Brunner et al. "Carbazole Compounds as Host Materials for Triplet Emitters in Organic Light-Emitting Diodes: Tuning the HOMO Level without Influencing the Triplet Energy in Small Molecules", Journal of American Chemical Society, vol. 126, No. 19, pp. 6035-6042 (2004).

Burnell et al., "Synthesis and Electrooptical Properties of Copolymers Derived from Phenol-Functionalized Telechelic Oligofluorenes", Macromolecules, vol. 38, pp. 10667 (2005).

Klapars et al. "A General and Efficient Copper Catalyst for the Amidation of Aryl Halides and the N-Arylation of Nitrogen Heterocycles", Journal of American Chemical Society, vol. 123, pp. 7727-7729 (2001).

Koene et al: "Asymmetric Triaryldiamines as Thermally Stable Hole Transporting Layers for Organic Light-Emitting Devices", Chemistry of Materials, vol. 10, pp. 2235-2250 (1998).

Louie et al. "The Largest Discrete Oligo(m-aniline). An Exponential Growth Strategy Using Palladium-Catalyzed Amination of Aryl Sulfonates", Macromolecules, vol. 31, pp. 6737-6739 (1998).

Yang et al. "Highly Efficient Single-layer Polymer Electrophosphorescent Devices", Advanced Materials, vol. 16, No. 2, pp. 160-166 (2004).

* cited by examiner

BIS-CARBAZOLE MONOMERS AND POLYMERS

BACKGROUND

The invention relates generally to compounds comprising bis-carbazole units that are difunctional. The invention also relates to monomers comprising bis-carbazole units and polymers, dendrimers and hyper-branched materials derived therefrom.

Organic light emitting devices (OLEDs), which make use of thin film materials that emit light when subjected to a voltage bias, are expected to become an increasingly popular form of flat panel display technology. This is because OLEDs have a wide variety of potential applications, including cellphones, personal digital assistants (PDAs), computer displays, informational displays in vehicles, television monitors, as well as light sources for general illumination. Due to their bright colors, wide viewing angle, compatibility with full motion video, broad temperature ranges, thin and conformable form factor, low power requirements and the potential for low cost manufacturing processes, OLEDs are seen as a future replacement technology for cathode ray tubes (CRTs) and liquid crystal displays (LCDs). Due to their high luminous efficiencies, OLEDs are seen as having the potential to replace incandescent, and perhaps even fluorescent, lamps for certain types of applications.

One approach to achieve full-color OLEDs includes energy transfer from host to emissive guest molecules. For this to be realized, the triplet energy state of the host has to be higher than the guest molecule. Carbazole derivatives have shown promise to perform well as host molecule in the presence of metal containing emissive guest molecules. Often used in this respect is poly(N-vinyl carbazole). However, quantum efficiencies of devices that use poly(N-vinyl carbazole) is still at the range of about 60 to 80%. Thus, there is a need in the art to develop OLEDs having device quantum efficiencies, while still maintaining the potential for the molecules to host red, green, and blue emissive complexes.

BRIEF DESCRIPTION

In one aspect, the invention relates to a compound of formula I

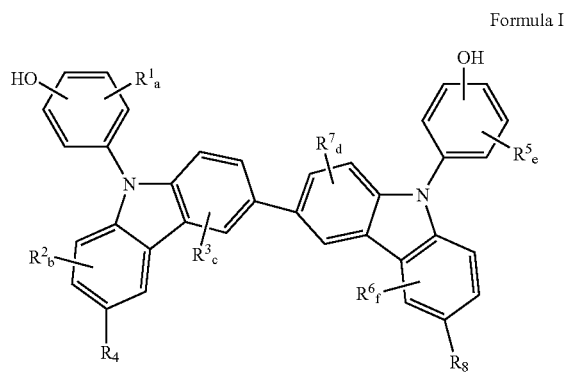

Formula I wherein $R^1$, $R^2$, $R^3$, $R^5$, $R^6$ and $R^7$ are independently at each occurrence a $C_1$-$C_{20}$ aliphatic radical, a $C_3$-$C_{20}$ aromatic radical, or a $C_3$-$C_{20}$ cycloaliphatic radical; $R^4$ and $R^8$ are independently at each occurrence a hydrogen, a $C_1$-$C_{20}$ aliphatic radical, a $C_3$-$C_{20}$ aromatic radical, or a $C_3$-$C_{20}$ cycloaliphatic radical;

a and e are independently at each occurrence 0, or an integer ranging from 1 to 4; and b, c, d and f are independently 0 or an integer ranging from 1 to 3.

In another aspect, the invention relates to a polymer comprising structural units of formula II

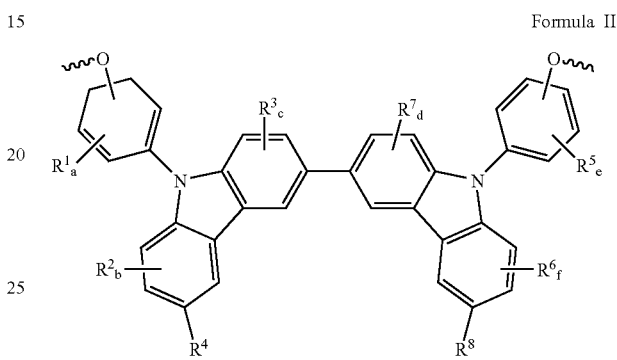

Formula II wherein $R^1$, $R^2$, $R^3$, $R^5$, $R^6$ and $R^7$ are independently at each occurrence a $C_1$-$C_{20}$ aliphatic radical, a $C_3$-$C_{20}$ aromatic radical, or a $C_3$-$C_{20}$ cycloaliphatic radical; $R^4$ and $R^8$ are independently at each occurrence a hydrogen, a $C_1$-$C_{20}$ aliphatic radical, a $C_3$-$C_{20}$ aromatic radical, or a $C_3$-$C_{20}$ cycloaliphatic radical;

a and e are independently at each occurrence 0, or an integer ranging from 1 to 4; and b, c, d and f are independently 0 or an integer ranging from 1 to 3.

In yet another aspect, the invention relates to a light emitting device comprising at least one electrode, at least one hole injection layer, at least one light emissive layer; wherein the light emissive layer comprises a polymer comprising structural units of formula II

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
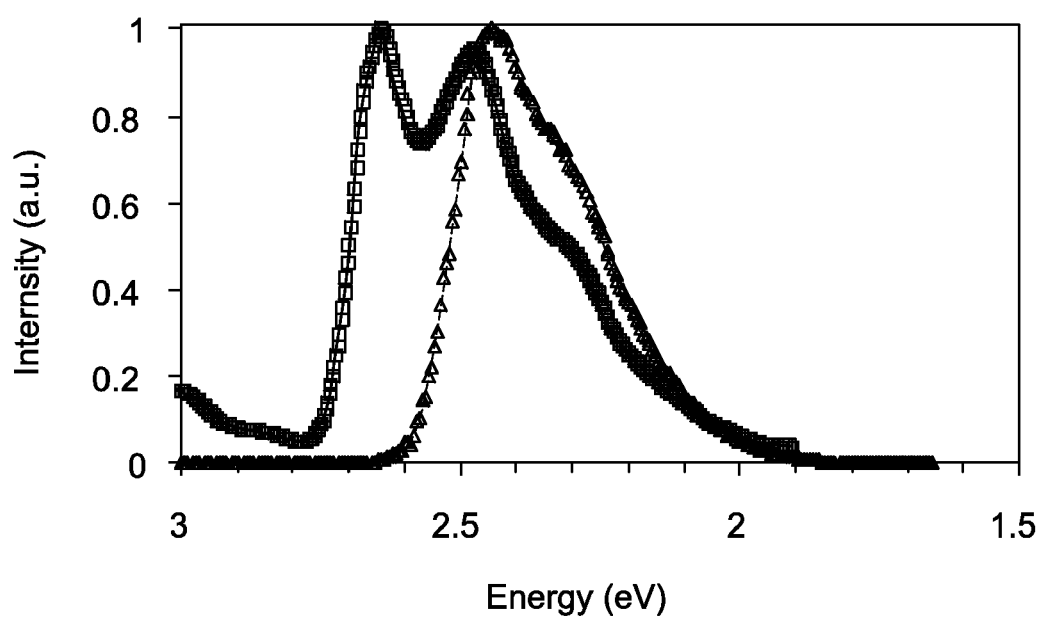
FIG. 1 shows the emission spectra of the samples from Example 5 and Comparative Example 5.

In one aspect, the invention relates to a compound comprising bis-carbazole units of formula I. Compounds of formula I may generally be regarded as bis-carbazole compounds. In some cases, the 3-, 6-, 3'-, 6'-positions may be susceptible to oxidative coupling reactions, and it may be advantageous to protect one or more of these positions. Thus, in some embodiments, $R^4$ and $R^8$ are t-butyl groups, while in still other embodiments, $R^4$ and $R^8$ are triarylsilyl groups, particularly triphenylsilyl, or trialkylsilyl groups, and in yet other embodiments, $R^4$ and $R^8$ are diphenyl phosphine oxide or diphenyl phosphine sulfide groups. A wide variety of groups may be used to substitute the bis-carbazole at the 6,6' positions, and these may include, but not limited to, methyl, ethyl, methoxy, tolyl, methylcyclohexyl, and halomethyl. In a particular aspect, the invention relates to a monomer of formula I, wherein b, c, d and f are all 0, which has the formula

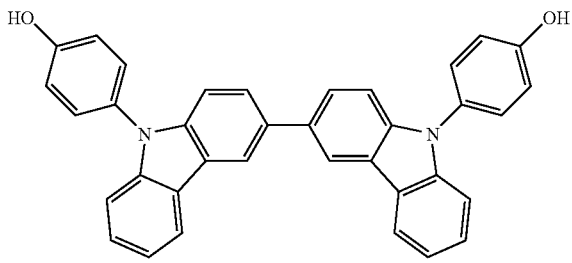

In another aspect, the present invention relates to polymers having structural units of formula II. The polymers are prepared by copolymerizing one or more monomers of formula I with one or more comonomers to result in polycarbonates, copolycarbonates, polyarylates, copolyarylates, copolyestercarbonates, polyethers, polyether sulfones, polyether imides, and combinations thereof, in the form of random, block or graft copolymers, or dendrimers or hyperbranched materials.

Accordingly, in some embodiments, the monomer of formula I may be copolymerized with phosgene, or phosgene and a bisphenol, or with a diaryl carbonate or bishaloformate to provide a polycarbonate. Exemplary monomers to make polycarbonates include diphenyl carbonate, bis(methylsalicyl) carbonate, bisphenol A bischloroformate, resorcinol bischloroformate, and combinations thereof. For example, copolymerization with phosgene and bisphenol A results in a polymer comprising structural units of formula

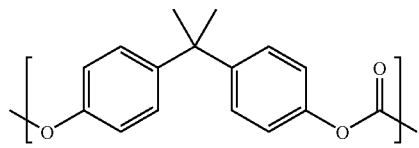

in addition to the structural units of formula II. Thus, in one particular embodiment, the resulting polymer comprises structural units of formula

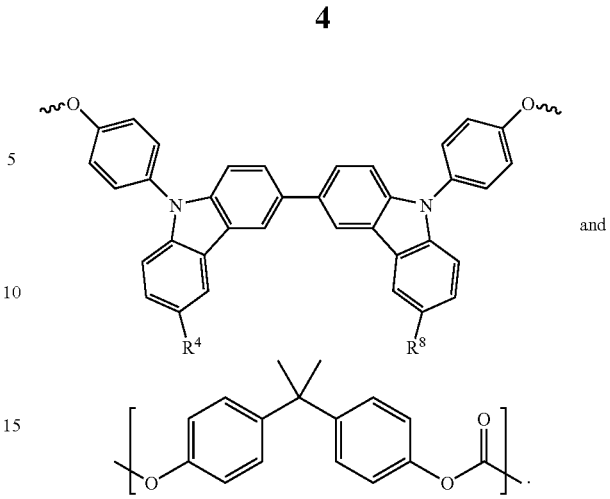

For example, a monomer of formula I may be reacted with bisphenol A and diphenyl carbonate in the presence of a minute amount of a basic catalyst such as sodium hydroxide at a temperature in a range between about 150 and 300° C. at subatmospheric pressure.

In other embodiments, the monomer of formula I may be copolymerized with a carboxylate ester, a carboxylic anhydride, or a carboxylic acid halide to yield a polyester. Exemplary comonomers that may be used to make polyesters include terephthaloyl chloride, terephthalic anhydride, naphthoic dianhydride, succinic anhydride, dimethyl oxalate, and combinations thereof.

In yet other embodiments, the monomer of formula I may be copolymerized with one or more dihaloarylsulfone monomer to yield a polyether sulfone. Dihaloarylsulfones may include bis(4-fluorophenyl)sulfone, bis(4-chlorophenyl)sulfone, 4,4'-bis((4-chlorophenyl)sulfonyl)-1,1-biphenyl and combinations thereof.

In other embodiments, the monomer of formula I may be copolymerized with one or more dihaloaryl monomers to yield a polyether. Exemplary dihaloaryl monomers include 1,6-dichlorobenzene, 4,4'-dichlorobiphenyl, 4,4'-dichlorodiphenylsulfide, 1,6-difluorobenzene, 4,4'-difluorobiphenyl, 4,4'-difluorodiphenylsulfie, and combinations thereof. For example, the monomer of formula I may be copolymerized with decafluorobiphenyl in N-methyl-2-pyrollidone (NMP), in the presence of a base such as potassium carbonate, at the temperature between about 100 and about 250° C.

In another embodiment, the monomer of formula I may be copolymerized with dihalobenzophenone monomer to yield a polyetherketone. Other dihalobenzophenone monomers include 1,4-bis(4'-chlorobenzoyl)benzene, 1,4-bis(4'-fluorobenzoyl)benzene, 1-(4'-chlorobenzoyl-4-(4"-fluorobenzoyl)benzene, and combinations thereof. For example, the monomer of formula I together with the disodium salt of bisphenol A may be reacted with 4,4'-dichlorobenzophenone in orthodichlorobenzene at a temperature between about 100 and about 250° C. in the presence of a phase transfer catalyst such as hexaethyl guanidinium chloride.

In another embodiment, the monomer of formula I may be copolymerized with a bis(halophthalimide) such as bis(4-chlorophthalimide) to obtain a polyetherimide. Other bis(halophthalimide)s include 1,3-bis[N-(4-fluorophthalimido)]benzene, 1,4-bis[N-(4-fluorophthalimido)]benzene, 1,3-bis[N-(3-fluorophthalimido)] benzene, 1,4-bis[N-(3-fluorophthalimido)] benzene, 4,4'-bis[N-(4-fluorophthalimido)]phenyl ether, 4,4'-bis[N-(3-fluorophthalimido)]phenyl ether, 4,4'-bis[N-(4-chlorophthalimido)]phenyl ether, 4,4'-bis[N-(3-chlorophthalimido)]phenyl ether, 1,3-bis[N-(4-chlorophthalimido)]benzene, 1,4-bis[N-(4-chlorophthalimido)]benzene, 1,3-bis[N-(3-chlorophthalimido)]benzene, 1,4-bis[N-(3-chlorophthalimido)]benzene, 1-[N-(4-chlorophthalimido)]-3-[N-(3-chlorophthalimido)benzene, 1-[N-(4-chlorophthalimido)]-4-[N-(3-chlorophthalimido)benzene, and combinations thereof.

Reaction conditions useful for the preparation of the polymers of the present invention include the use of polar solvents and bases of suitable strength. Exemplary solvents include chloroform, methylene chloride, orthodichlorobenzene, veratrole, anisole, and combinations thereof. Exemplary bases include triethylamine, sodium hydroxide, potassium hydroxide, and combinations thereof. Suitable catalysts may also be employed to effect the polymerization reaction.

In certain embodiments, the polymerization reaction may be conducted at a suitable temperature that ranges from about room temperature to about the boiling point of the solvent of choice. The polymerization may also be conducted at atmospheric pressure, subatmospheric pressures, or superatmospheric pressures. The polymerization reaction is conducted for a time period necessary to achieve polymer of a suitable molecular weight. The molecular weight of a polymer is determined by any of the techniques known to those skilled in the art, and include viscosity measurements, light scattering, and osmometry. The molecular weight of a polymer is typically represented as a number average molecular weight $M_n$, or weight average molecular weight, $M_w$. A particularly useful technique to determine molecular weight averages is gel permeation chromatography (GPC), from wherein both number average and weight average molecular weights are obtained. Molecular weight of the polymers is not critical, and in some embodiments, polymers of $M_w$ greater than 30,000 grams per mole (g/mol) are desirable, in other embodiments, polymers of $M_w$ greater than 50,000 g/mol are desirable, while in yet other embodiments, polymer of $M_w$ greater than 80,000 g/mol are desirable.

The polymerization reaction may be controlled the addition of a suitable monofunctional reactant, sometimes also referred to in the art as "end-capping agents", or "chain stoppers". The chain stopper serves to limit polymer molecular weight. Suitable phenolic chain stoppers include phenol and p-cumylphenol. Suitable aromatic halide chain stoppers include, 4-chlorophenyl phenyl sulfone, 4-fluorophenyl phenyl sulfone, and 4-chlorophenyl phenyl ketone.

Polymers provided in the present invention may find use in a wide variety of applications that include, but are not limited to, light emitting electrochemical cells, photo detectors, photo conductive cells, photo switches, and display devices. Thus, in one aspect, the invention relates to a light emitting comprising at least one electrode, at least one hole injection layer, at least one light emissive layer; wherein the light emissive layer comprises a polymer comprising structural units of formula II.

An organic light emitting device typically comprises multiple layers which include in the simplest case, an anode layer and a corresponding cathode layer with an organic electroluminescent layer disposed between said anode and said cathode. When a voltage bias is applied across the electrodes, electrons are injected by the cathode into the electroluminescent layer while electrons are removed from (or "holes" are "injected" into) the electroluminescent layer from the anode. Light emission occurs as holes combine with electrons within the electroluminescent layer to form singlet or triplet excitons, light emission occurring as singlet excitons transfer energy to the environment by radiative decay.

Other components which may be present in an organic light emitting device in addition to the anode, cathode and light emitting material include hole injection layers, electron injection layers, and electron transport layers. The electron transport layer need not be in contact with the cathode, and frequently the electron transport layer is not an efficient hole transporter and thus it serves to block holes migrating toward the cathode. During operation of an organic light emitting device comprising an electron transport layer, the majority of charge carriers (i.e. holes and electrons) present in the electron transport layer are electrons and light emission can occur through recombination of holes and electrons present in the electron transport layer. Additional components which may be present in an organic light emitting device include hole transport layers, hole transporting emission (emitting) layers and electron transporting emission (emitting) layers.

Compounds of formula I have triplet energy states that are useful in applications such as organic light emitting devices (OLEDs), as they may give rise to highly efficient devices. Further, the triplet energy of these compounds may be high enough that it may be greater than those of guest dyes used in devices, and thus may serve as host molecules. The compounds of the present invention are particularly well suited for use in hole transport layers in organic light emitting devices. In one embodiment, the present invention relates to an organic light emitting device comprising the compounds as a constituent of a hole transport layer of an organic light emitting device.

The organic electroluminescent layer is a layer within an organic light emitting device which when in operation contains a significant concentration of both electrons and holes and provides sites for exciton formation and light emission. A hole injection layer is a layer in contact with the anode which promotes the injection of holes from the anode into the interior layers of the OLED; and an electron injection layer is a layer in contact with the cathode that promotes the injection of electrons from the cathode into the OLED; an electron transport layer is a layer which facilitates conduction of electrons from cathode to a charge recombination site. The electron transport layer need not be in contact with the cathode, and frequently the electron transport layer is not an efficient hole transporter and thus it serves to block holes migrating toward the cathode. During operation of an organic light emitting device comprising an electron transport layer, the majority of charge carriers (i.e. holes and electrons) present in the electron transport layer are electrons and light emission can occur through recombination of holes and electrons present in the electron transport layer. A hole transport layer is a layer which when the OLED is in operation facilitates conduction of holes from the anode to charge recombination sites and which need not be in contact with the anode. A hole transporting emission layer is a layer in which when the OLED is in operation facilitates the conduction of holes to charge recombination sites, and in which the majority of charge carriers are holes, and in which emission occurs not only through recombination with residual electrons, but also through the transfer of energy from a charge recombination zone elsewhere in the device. An electron transporting emission layer is a layer in which when the OLED is in operation facilitates the conduction of electrons to charge recombination sites, and in which the majority of charge carriers are electrons, and in which emission occurs not only through recombination with residual holes, but also through the transfer of energy from a charge recombination zone elsewhere in the device.

Materials suitable for use as the anode include materials having a bulk conductivity of at least about 100 ohms per square, as measured by a four-point probe technique. Indium tin oxide (ITO) is frequently used as the anode because it is substantially transparent to light transmission and thus facilitates the escape of light emitted from electro-active organic layer. Other materials which may be utilized as the anode layer include tin oxide, indium oxide, zinc oxide, indium zinc oxide, zinc indium tin oxide, antimony oxide, and mixtures thereof.

Materials suitable for use as the cathode include by zero valent metals which can inject negative charge carriers (electrons) into the inner layer(s) of the OLED. Various zero valent metals suitable for use as the cathode 20 include K, Li, Na, Cs, Mg, Ca, Sr, Ba, Al, Ag, Au, In, Sn, Zn, Zr, Sc, Y, elements of the lanthanide series, alloys thereof, and mixtures thereof. Suitable alloy materials for use as the cathode layer include Ag—Mg, Al—Li, In—Mg, Al—Ca, and Al—Au alloys. Layered non-alloy structures may also be employed in the cathode, such as a thin layer of a metal such as calcium, or a metal fluoride, such as LiF, covered by a thicker layer of a zero valent metal, such as aluminum or silver. In particular, the cathode may be composed of a single zero valent metal, and especially of aluminum metal.

Light emitting devices according to the present invention include polymers having formula IV in the hole injection layer. The polymers may be used in place of, or in addition to traditional materials such as poly(3,4-ethylenedioxythiophene), which is commercially available from H.C. Stark, Inc. under the BAYTRON® tradename, and polymers based on the thieno[3,4b]thiophene (TT) monomer, commercially available from Air Products Corporation. In particular, the polymers may be blended with PEDOT to form a hole injection layer.

Materials suitable for use in hole transporting layers include 1,1-bis((di-4-tolylamino) phenyl)cyclohexane, N,N'-bis(4-methylphenyl)-N,N'-bis(4-ethylphenyl)-(1,1'-(3, 3'-dimethyl)biphenyl)-4,4'-diamine, tetrakis-(3-methylphenyl)-N,N,N',N'-2,5-phenylenediamine, phenyl-4-N,N-diphenylaminostyrene, p-(diethylamino) benzaldehyde diphenylhydrazone, triphenylamine, 1-phenyl-3-(p-(diethylamino) styryl)-5-(p-(diethylamino)phenyl)pyrazoline, 1,2-trans-bis(9H-carbazol-9-yl)cyclobutane, N,N,N',N'-tetrakis (4-methylphenyl)-(1,1'-biphenyl)-4,4'-diamine, copper phthalocyanine, polyvinylcarbazole, (phenylmethyl)polysilane; poly(3,4-ethylendioxythiophene) (PEDOT), polyaniline, polyvinylcarbazole, triaryldiamine, tetraphenyldiamine, aromatic tertiary amines, hydrazone derivatives, carbazole derivatives, triazole derivatives, imidazole derivatives, oxadiazole derivatives having an amino group, and polythiophenes as disclosed in U.S. Pat. No. 6,023,371.

Materials suitable for use as the electron transport layer include poly(9,9-dioctyl fluorene), tris(8-hydroxyquinolato) aluminum ($Alq_3$), 2,9-dimethyl-4,7-diphenyl-1,1-phenanthroline, 4,7-diphenyl-1,10-phenanthroline, 2-(4-biphenylyl)-5-(4-t-butylphenyl)-1,3,4-oxadiazole, 3-(4-biphenylyl)-4-phenyl-5-(4-t-butylphenyl)-1,2,4-triazole, 1,3,4-oxadiazole-containing polymers, 1,3,4-triazole-containing polymers, quinoxaline-containing polymers, and cyano-PPV.

Materials suitable for use in the light emitting layer include electroluminescent polymers such as poly(9,9-dioctyl fluorene) and copolymers thereof, such as F8-TFB.

In one aspect, polymers comprising structural units of formula II may form part of the hole collection layer, while in another aspect, polymers comprising structural units of formula II form part of the hole injection layer. Thus, in one aspect, the present invention relates to more efficient organic light emitting devices comprising polymers comprising structural units of formula II.

DEFINITIONS

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), and anthraceneyl groups (n=3). The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC($CF_3)_2$PhO—), 4-chloromethylphen-1-yl, 3-trifluorovinyl-2-thienyl, 3-trichloromethylphen-1-yl (i.e., 3-$CCl_3$Ph-), 4-(3-bromoprop-1-yl)phen-1-yl (i.e., 4-BrCH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2)_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g. methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}C(CF_3)_2C_6H_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. $CH_3CHBrCH_2C_6H_{10}O$—), and the like. Further examples of cycloaliphatic radicals include 4-allyloxycyclohex-1-yl, 4-aminocyclohex-1-yl (i.e., $H_2C_6H_{10}$—), 4-aminocarbonylcyclopent-1-yl (i.e., $NH_2COC_5H_8$—), 4-acetyloxycyclohex-1-yl, 2,2-dicyanoisopropylidenebis(cyclohex-4-yloxy) (i.e., —$OC_6H_{10}C(CN)_2C_6HoO$—), 3-methylcyclohex-1-yl, methylenebis(cyclohex-4-yloxy) (i.e., —$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —$OC_6H_{10}(CH_2)_6C_6H_{10}O$—), 4-hydroxymethylcyclohex-1-yl (i.e., 4-$HOCH_2C_6H_{10}$—), 4-mercaptomethylcyclohex-1-yl (i.e., 4-$HSCH_2C_6H_{10}$—), 4-methylthiocyclohex-1-yl (i.e., 4-$CH_3SC_6H_{10}$—), 4-methoxycyclohex-1-yl, 2-methoxycarbonylcyclohex-1-yloxy (2-$CH_3OCOC_6H_{10}O$—), 4-nitromethylcyclohex-1-yl (i.e., $NO_2CH_2C_6H_{10}$—), 3-trimethylsilylcyclohex-1-yl, 2-t-butyldimethylsilylcyclopent-1-yl, 4-trimethoxysilylethylcyclohex-1-yl (e.g. $(CH_3O)_3SiCH_2CH_2C_6H_{10}$—), 4-vinylcyclohexen-1-yl, vinylidenebis(cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" organic radicals substituted with a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g. —$CH_2CHBrCH_2$—), and the like. Further examples of aliphatic radicals include allyl, aminocarbonyl (i.e., —$CONH_2$), carbonyl, 2,2-dicyanoisopropylidene (i.e., —$CH_2C(CN)_2CH_2$—), methyl (i.e., —$CH_3$), methylene (i.e., —$CH_2$—), ethyl, ethylene, formyl (i.e. —CHO), hexyl, hexamethylene, hydroxymethyl (i.e. —$CH_2OH$), mercaptomethyl (i.e., —$CH_2SH$), methylthio (i.e., —$SCH_3$), methylthiomethyl (i.e., —$CH_2SCH_3$), methoxy, methoxycarbonyl (i.e., $CH_3OCO$—), nitromethyl (i.e., —$CH_2NO_2$), thiocarbonyl, trimethylsilyl (i.e., $(CH_3)_3Si$—), t-butyldimethylsilyl, 3-trimethyoxysilylpropyl (i.e., $(CH_3O)_3SiCH_2CH_2CH_2$—), vinyl, vinylidene, and the like. By way of further example, a $C_1$-$C_{10}$ aliphatic radical contains at least one but no more than 10 carbon atoms. A methyl group (i.e., $CH_3$—) is an example of a $C_1$ aliphatic radical. A decyl group (i.e., $CH_3(CH_2)_9$—) is an example of a $C_{10}$ aliphatic radical.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

EXAMPLES

Polystyrene (PS) used in the triplet measurements was a GPC standard having weight average molecular weight of 18,700 and was obtained from Aldrich Chemical Co., Milwaukee, Wis., USA. A green phosphorescent dye, tris(2-(4-tolyl)phenylpyridine)iridium, [Ir(mppy)$_3$] was purchased from American Dye Sources, Canada and used as received. Glass pre-coated with indium tin oxide (ITO) (Applied Films). Poly (3,4-ethylendioxythiophene/polystyrene sulfonate (PEDOT:PSS) was purchased from H.C. Starck Co., GmbH, Leverkusen, Germany. N,N'-diphenyl-N-N"-(bis(3-methylphenyl)-[1,1-biphenyl]-44-diamine (TPD) and 2-(4-biphenyllyl)-5-(4-tert-butylphenyl)-1,3,4-oxadiazole (PBD) was used as a hole injection material and an electron injection material, respectively. Both TPD and PBD were purchased from Aldrich and used as received. All other chemicals and reagents are obtained from Aldrich Chemical Co., Milwaukee, Wis., USA. Flash chromatography was carried out by Fisher Scientific (100-200 mesh) or Aldrich (60-350 mesh) silica gel, prepacked silical gel coumn by Isco. Thin layer chromatography was carried out on commercially available pre-coated glass plates (Analtech, GF, 250 microns).

General Methods

Molecular weights were determined relative to polystyrene standards on a Perkin Elmer Series 200 GPC equipped with a Polymer Laboratories size exclusion column (PLgel 5 μm MIXED-C, 300×7.5 mm kept at 40° C.) using chloroform with 3.6% v/v isopropanol as the mobile phase. NMR spectra were measured on a Bruker 400 or Bruker Advance 500 spectrometers.

Synthesis

The synthesis of the bis(9-(hydroxyphenyl)carbazol-3-yl) was done in a three-step process as shown in scheme 1. This was achieved by the addition of p-bromoanisole to carbazole followed by coupling of the N-(4-methoxyphenyl) carbazole using FeCl$_3$ catalyst, and finally deprotecting the methoxy group to give rise to the dihydroxy compound.

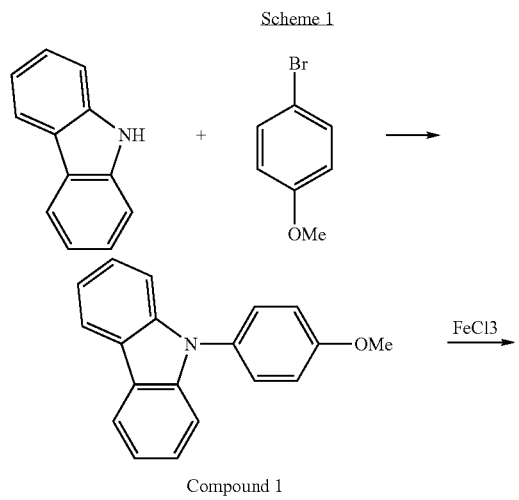

Scheme 1

Compound 1

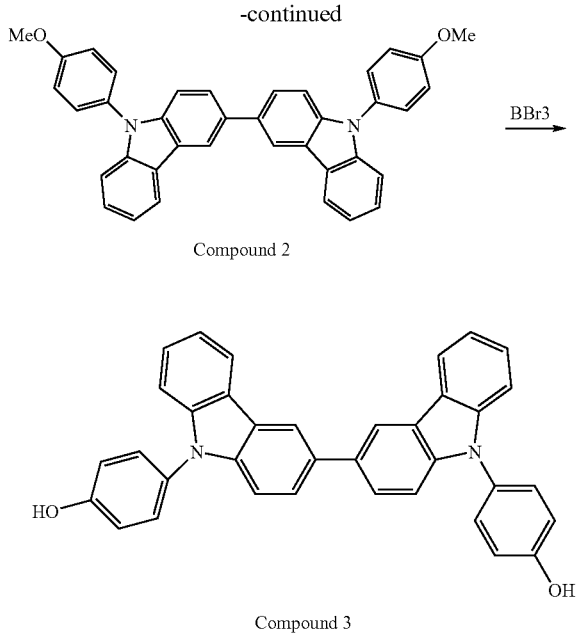

Compound 2

Compound 3

Example 1

Synthesis of Compound 19-(4-methoxyphenyl)-carbazole

Method 1: A flask containing a mixture of 5.025 g (0.03 mol) carbazole, 7.3 g (0.04 mol) 4-bromoanisole, 12.5 g (0.09 mol) K$_2$CO$_3$ in 200 ml toluene was evacuated and charged with argon for three times, after which 2 mol % Pd(OAc)$_2$ and 0.1 g tris(t-butyl)phosphine were added. The mixture was stirred for one week under argon. Fresh Pd(OAc)$_2$ and Pt(t-Bu)$_3$ were added after two days. After the mixture was allowed to cool and water was added. The organic layer was separated, dried over MgSO$_4$, and concentrated. After column chromatography, white crystals were obtained.

Method 2: To a three neck round bottom flask, was charged bromoanisole (18.7 g, 100 mmol), carbazole (16.7 mg, 100 mmol), potassium phosphate (21 g, 154 mmol) and copper iodide (1 g, 5 mmol). Dioxane (400 ml) was added and subsequently, the reaction flask was flushed with N$_2$. Dimethylethylene diamine (1 g, 5 mmol) was then added to the reaction flask via syringe. The reaction mixture was then heated at 95° C. for 24 h under nitrogen. Then, the solution was cooled down to room temperature, and 50 mL of H$_2$O was added. The reaction mixture was extracted with methylene chloride and the organic and aqueous phase was separated. The organic phase was further washed twice with 50 mL of water and once with 50 mL of brine and dried over Na$_2$SO$_4$. The solvent was removed under vacuum to afford the crude product. Recrystallization from methanol gave 17.99 g of white crystals of compound 1. $^1$H NMR (CDCl$_3$) δ 8.17 (d, 2H), 7.48 (d, 2H), 7.43 (dt, 2H), 7.36 (d, 2H), 7.31 (dt, 2H), 7.14 (d, 2H), 3.96 (s, 3H). $^{13}$C NMR (CDCl$_3$): δ 159, 141, 130, 129, 126, 123, 120, 120, 115, 110, 56. EI-MS: 273(M+), 258.

Example 2

Synthesis of Compound 2 bis(9-(4-methoxyphenyl)carbazol-3-yl)

To a stirred solution of 8.03 g (29.4 mmol) of compound 1 in 500 mL chloroform under argon atmosphere was added at once 9.67 g (59.6 mmol) of iron(III) chloride. After stirring at room temperature for 40 hours, 250 mL of water was added. The organic layer was separated was extracted thrice with 250 mL of water and filtered through a pad of basic alumina. Then, a small amount of methylene chloride was used to rinse the pad. The filtrate was dried over $Na_2SO_4$, filtered and concentrated under vacuum. The mixture was purified by recrystallizing from THF/hexanes to afford the product compound 2 as white crystals at 52% yield. $^1$H NMR ($CDCl_3$): d 8.49 (d, 2H), 8.28 (d, 2H), 7.81 (dd, 2H), 7.54 (d, 4H), 7.47 (d, 2H), 7.46 (dt, 2H), 7.40 (d, 2H), 7.35 (dt, 2H), 7.18 (d, 4H), 3.97 (s, 6H). $^{13}$C NMR ($CDCl_3$): d 159, 142, 141, 134, 130, 129, 126, 126, 124, 123, 120, 120, 119, 115, 110, 110, 56. EI-MS (M+): 544.

Example 3

Synthesis of Compound 3 bis(9-(hydroxyphenyl)carbazol-3-yl)

0.544 g of compound 2 (1 mmol) was added to a 15 mL of anhydrous $CH_2Cl_2$ in a 50 mL round-bottom flask and stirred with a magnetic stir bar. Solution was cooled in an ice-bath to 0° C. under a nitrogen atmosphere. Boron tribromide (2.4 mmol, 2.4 mL 1M in $CH_2Cl_2$) was added via syringe dropwise to solution. The flask was removed from the ice-bath and allowed to equilibrate to room temperature, followed by one hour of stirring. The solution was decanted into 10 mL of ice water in a 50 mL beaker. After 30 minutes of hydrolysis with stirring, the organic layer was extracted with 2×10 mL of $CH_2Cl_2$. The organic layer was washed with 2×15 mL of cold water to neutralize any excess $BBr_3$. Solution was dried with sodium sulfate and the solvent was evaporated using a rotary evaporator to afford 0.46 g (90%) solid. Recrystallization from THF/hexanes afforded 0.346 g of product used in the following polymerization. $^1$H NMR ($CDCl_3$): d 8.47 (b, 2H), 8.26 (d, 2H), 7.79 (dd, 2H), 7.49 (d, 4H), 7.45 (d, 2H), 7.38 (dt, 2H), 7.33 (d, 2H), 7.10 (d, 4H). EI-MS (M+): 516.

Example 4

Polymerization of bis(9-(hydroxyphenyl)carbazol-3-yl) with BPA-Bis-chloroformate A dry reaction vessel equipped with a magnetic stirring bar under nitrogen atmosphere, charged with compound 3 bis(9-(hydroxyphenyl)carbazol-3-yl) (0.346 g, 0.6697 mmol), BPA-bischloroformate (0.237 g, 0.6697 mmol), and 8 mL of dry methylene chloride. The resulting milky solution was immersed in an ice-salt bath for 15 minutes and then charged with 0.25 mL (1.79 mmol) of dry triethylamine. The mixture was maintained at 0-5° C. with stirring for 1 h, allowed to warm to room temperature, and stirred for an additional hour. Then the mixture was diluted with 5 mL $CH_2Cl_2$, 1.0 mL of 10% $NaHCO_3$ was added, and the mixture was stirred for 10 min and then transferred to a separatory funnel. The aqueous phase was discarded and the organic phase was washed successively with equal volumes of 1 N HCl (1×) and water (2×). The solution was concentrated to 4 mL and then precipitated into 40 mL of methanol. The collected polymer was redissolved in 10 mL of $CH_2Cl_2$ and this solution was added slowly to 1000 mL of boiling, deionized water. The solids were again collected, air-dried, redissolved in fresh $CH_2Cl_2$ (12 mL) and reprecipitated again into methanol. The resulting polymer was dried at 80° C. in a vacuum oven overnight. GPC (Gel permeation chromatography) analysis showed the polymer had a weight average molecular weight Mw of 31,500k, and a polydispersity index PDI of 3.18.

Triplet Energy Levels Characterization

The triplet energy levels were obtained using a Perkin Elmer LS55 spectro-fluorimeter equipped with an uncooled R928 red sensitive photo multiplier tube. The typical procedure was to place a sample in a clean laboratory mortar and immerse the sample in liquid nitrogen at least 2 minutes prior to the measurement to ensure thermal equilibrium. Then the sample was optically excited. Emission spectra were obtained by using the delayed collection feature of the LS55, in which the detection is gated at time delayed from the initial 20 μs excitation pulse.

Example 5

Bis(9-(hydroxyphenyl)carbazol-3-yl) Containing Sample Preparation for Triplet Energy Characterization The sample for triplet energy levels was prepared in the following manner: 10 mg of bis[9-(hydroxyphenyl)carbazol-3-yl] was dissolved in 1 ml anhydrous THF. The solution was then spin-coated onto a pre-cleaned quartz substrate.

Comparative Example 1

Ir(mppy)$_3$ Containing Sample for Triplet Energy Characterization

The sample for triplet energy levels was prepared in the following manner: A mixture of 1 wt % tris(2-(4-tolyl)phenylpyridine)iridium (Ir(mppy)$_3$) in polystyrene (PS) was prepared by mixing of 0.010 ml of 1 wt % Ir(mppy)$_3$ (10 mg of Ir(mppy)$_3$ in 1 ml THF) with 1.0 ml of 1 wt % PS in THF, which was then spin-coated onto a pre-cleaned quartz substrate.

FIG. 1 shows the emission spectra of the two samples. The sample from Example 5 has a greater triplet energy level relative to the sample from Comparative Example 1. For instance, the first emission peak of the sample from Example 5 appears at 2.7 eV relative to the 2.4 eV of the sample from Comparative Example 1. Lifetime of triplet excited states of Ir(mppy)$_3$ in the presence and absence of Compound 3

The lifetime of triplet excited states were measured using an Edinburgh CD920 spectrometer equipped with a cooled R928 photo multiplier tube. The typical procedure was to place a sample in a vacuum dewer and then pump down to $4*10E^{-5}$ torr. Then the sample was optically excited at 394 nm with a pulsed diode laser (class HIB, 390-420 nm, maximum power of 5 mW). Time resolved emission spectra were measured at 540 nm.

Example 6

Bis(9-(hydroxyphenyl)carbazol-3-yl)-Containing Sample Preparation for Lifetime of Triplet Excited States Characterization A mixture of 1 wt % Ir(mppy)$_3$ in bis[9-(hydroxyphenyl) carbazol-3-yl] was prepared by mixing 0.010 ml of 1 wt % Ir(mppy)$_3$ (10 mg of Ir(mppy)$_3$ in 1 ml THF) with 1.0 ml of 1 wt % bis[9-(hydroxyphenyl)carbazol-3-yl] in THF. The solution was then spin-coated onto a pre-cleaned quartz substrate.

Comparative Example 2

Polystyrene Containing Sample Preparation for Lifetime of Triplet Excited States Characterization A mixture of 1 wt % Ir(mppy)$_3$ in polystyrene was prepared by mixing 0.010 ml of 1 wt % Ir(mppy)$_3$ (10 mg of Ir(mppy)$_3$ in 1 ml THF) with 1.0 ml of 1 wt % PS in THF. The solution was spin-coated onto a pre-cleaned quartz substrate.

Figure 2:
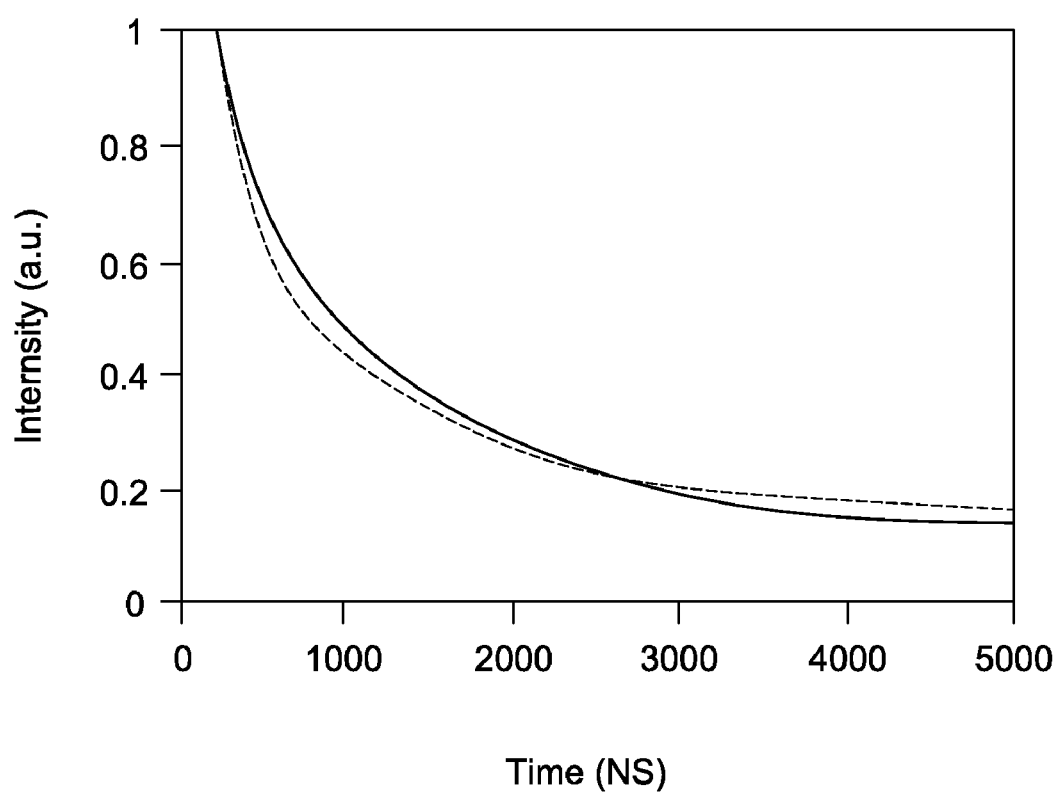
FIG. 2 shows the triplet excited states decay profiles of the phosphorescent dye in the presence and absence of bis(9-(hydroxyphenyl)carbazol-3-yl).

FIG. 2 shows the triplet excited states decay profiles of the phosphorescent dye in the presence and absence of bis(9-(hydroxyphenyl)carbazol-3-yl). The phosphorescent dye had comparable triplet decay profiles (equivalently lifetimes) when dispersed in bis(9-(hydroxyphenyl)carbazol-3-yl) relative to an insulating polystyrene matrix. The data is consistent with data obtained from triplet energy measurements and suggests that there is no energy transfer from the dye [Ir(mppy)$_3$] to the host {either PS or bis[9-(hydroxyphenyl)carbazol-3-yl]}. Thus, bis[9-(hydroxyphenyl)carbazol-3-yl] is suitable as a host material for Ir(mppy)$_3$ in phosphorescent OLEDs.

Example 7

OLED Device Fabrication and Characterization

Glass pre-coated with indium tin oxide (ITO) was used as the substrate. A layer (c.a. 65 nm) of poly (3,4-ethylendioxythiophene/polystyrene sulfonate (PEDOT:PSS), was deposited onto ultraviolet-ozone treated ITO substrates via spin-coating and then baked for 1 hour at 180° C. in air. N,N'-diphenyllyl-N-N'''-bis(3-methylphenyl)-[1,1-biphenyl]-4,4'-diamine (TPD) and 2-(4-biphenyllyl)-5-(4-tert-butylphenyl)-1,3,4-oxadiazole (PBD) was used as a hole injection material and an electron injection material, respectively. A mixture solution of bis[9-(hydroxyphenyl)carbazol-3-yl]: PBD:TPD:Ir(mppy)$_3$ (61:24:9:6) was prepared by mixing 1.220 ml of 1.5 wt % of bis[9-(hydroxyphenyl)carbazol-3-yl] in chlorobenzene (CB), 0.240 ml of 3.0 wt % of PBD in CB, 0.090 ml of 3.0 wt % TPD in CB and 0.18 ml of 1 wt % of Ir(mppy)$_3$ in CB. Then the mixture solution was spin-coated onto the PEDOT:PSS and then baked at 70° C. for 10 mins. The device fabrication was finished with the deposition of a CsF (4 nm)/Al (100 nm) via thermal evaporation at a based pressure of 2*10E-6 Torr. Following metal evaporation, the devices were encapsulated using a glass slide sealed with an optical adhesive (Norland® 68, obtained from Norland Products Inc, New Jersey, U.S.A.

Figure 3:
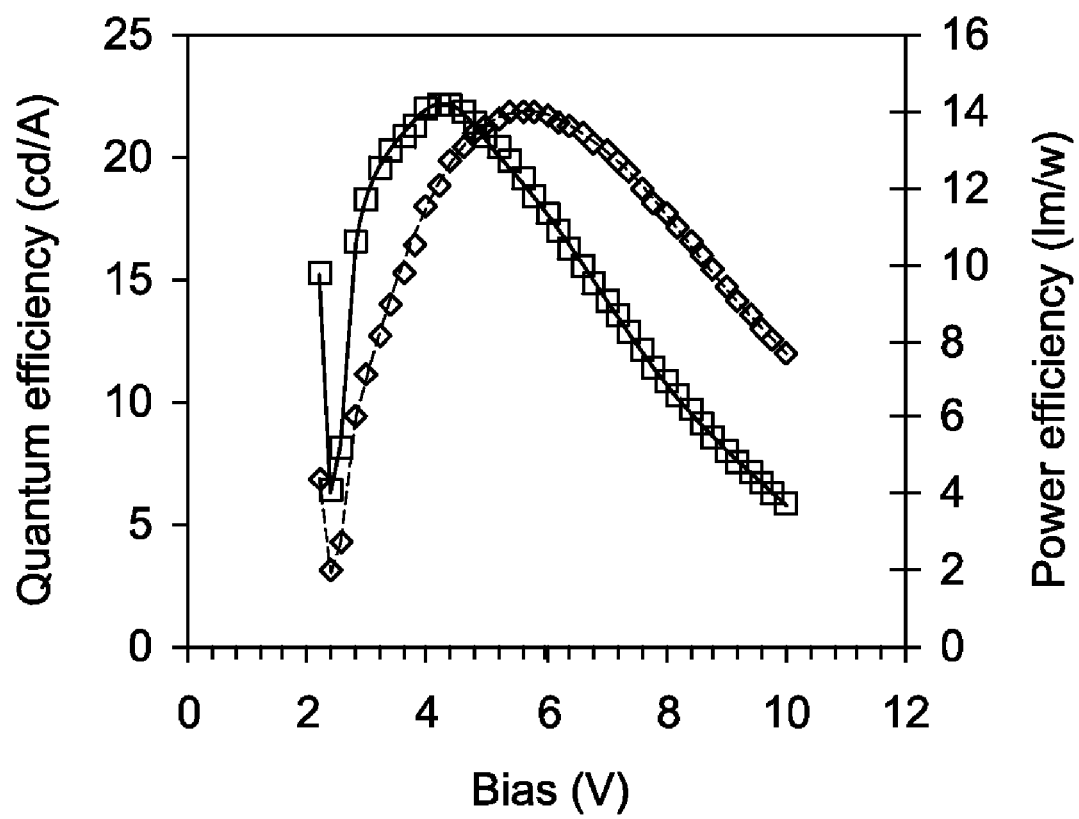
FIG. 3 shows a plot of quantum efficiency (cd/A) and a plot of power efficiency (1 m/w) as a function of bias voltage (V) for the exemplary OLED devices.

Performance of OLEDs was characterized by measuring current-voltage-luminance (I-V-L) characteristics. A photo-diode calibrated with a luminance meter (Minolta LS-110) was used to measure the luminance (in units of candela per square meter, cd/m2). FIG. 3 shows that the maximum quantum efficiency, represented by diamonds, is 21.9 cd/A, and the maximum power efficiency, represented by squares, achieved was 14.2 µm/w. This is comparable to the state-of-the-art (27 cd/A and 14.1 µm/w) polymeric phosphorescent device as described in X. H. Yang, D. Neher, D. Hertel and T. K. Daubler, "Highly efficient single-layer polymer electrophosphorescent devices", Adv. Mater. Vol 16, pp 161-166, 2004.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A polymer comprising structural units of formula II

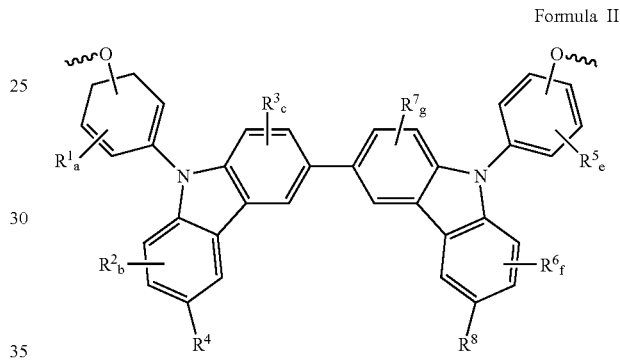

Formula II wherein
$R^1$, $R^2$, $R^3$, $R^5$, $R^6$ and $R^7$ are independently at each occurrence a $C_1$-$C_{20}$ aliphatic radical, a $C_3$-$C_{20}$ aromatic radical, or a $C_3$-$C_{20}$ cycloaliphatic radical; $R^4$ and $R^8$ are independently at each occurrence a hydrogen, a $C_1$-$C_{20}$ aliphatic radical, a $C_3$-$C_{20}$ aromatic radical, or a $C_3$-$C_{20}$ cycloaliphatic radical;

a and e are independently at each occurrence 0, or an integer ranging from 1 to 4;

b, c, d and f are independently 0 or an integer ranging from 1 to 3.

2. The polymer of claim 1, which is a polyester.

3. The polymer of claim 1, which is a polyether.

4. The polymer of claim 1, which is a polycarbonate.

5. The polymer of claim 1, which is a polyestercarbonate.

6. The polymer of claim 1, which is a polyetherimide.

7. The polymer of claim 1, which is a polyaryletherketone.

8. The polymer of claim 1, which is a polyarylethersulfone.

9. The polymer of claim 1, wherein $R^4$ and $R^8$ are independently selected from the group consisting of hydrogen, triarylsilyl, trialkylsilyl, t-butyl, diphenyl phosphine oxide, diphenyl phosphine sulfide, and combinations thereof.

10. The polymer of claim 1, wherein a and e are 0.

11. The polymer of claim 1, wherein b, c, d and f are 0.

12. The polymer of claim 1, of formula

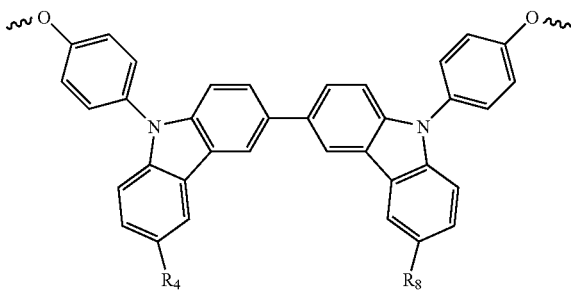

wherein $R^4$ and $R^8$ independently selected from the group consisting of hydrogen, triarylsilyl, trialkylsilyl, t-butyl, diphenyl phosphine oxide, diphenyl phosphine sulfide, and combinations thereof.

13. The polymer of claim 1, of formula

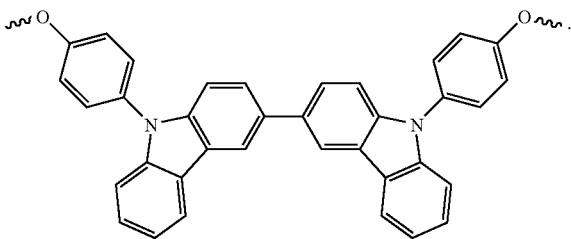

14. The polymer of claim 1, additionally comprising structural units of formula

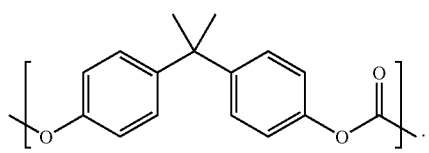

15. A light emitting device comprising at least one electrode,
at least one hole injection layer,
at least one light emissive layer;
wherein the light emissive layer comprises a polymer comprising structural units of formula II Formula II

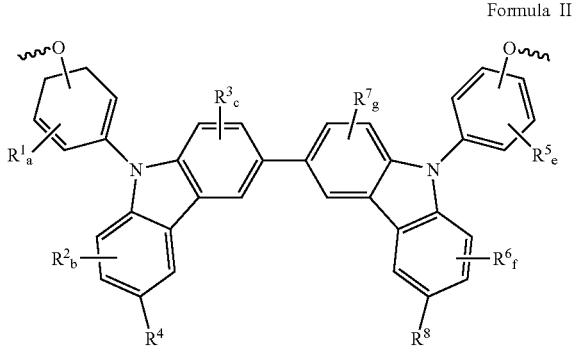

$R^1$, $R^2$, $R^3$, $R^5$, $R^6$ and $R^7$ are independently at each occurrence a $C_1$-$C_{20}$ aliphatic radical, a $C_3$-$C_{20}$ aromatic radical, or a $C_3$-$C_{20}$ cycloaliphatic radical; $R^4$ and $R^8$ are independently at each occurrence a hydrogen, a $C_1$-$C_{20}$ aliphatic radical, a $C_3$-$C_{20}$ aromatic radical, or a $C_3$-$C_{20}$ cycloaliphatic radical;

a and e are independently at each occurrence 0, or an integer ranging from 1 to 4;

b, c, d and f are independently 0 or an integer ranging from 1 to 3.

16. The light emitting device of claim 15, wherein the polymer is a polyester.

17. The light emitting device of claim 15, wherein the polymer is a polyether.

18. The light emitting device of claim 15, wherein the polymer is a polycarbonate.

19. The light emitting device of claim 15, wherein the polymer is a polyetherimide.

20. The light emitting device of claim 15, wherein the polymer is a polyarylethersulfone.

21. The light emitting device of claim 15, wherein the polymer is a polyaryletherketone.

22. The light emitting device of claim 15, wherein $R^4$ and $R^8$ are independently selected from the group consisting of hydrogen, triarylsilyl, trialkylsilyl, t-butyl, diphenyl phosphine oxide, diphenyl phosphine sulfide, and combinations thereof.

23. The light emitting device of claim 15, wherein a and e are 0.

24. The light emitting device of claim 15, wherein b, c, d and f are 0.

25. The light emitting device of claim 15, wherein the emissive layer comprises a polymer comprising structural units of formula

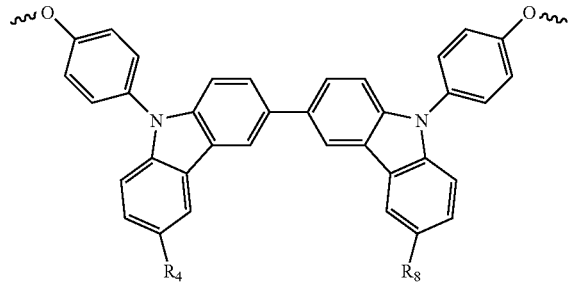

wherein $R^4$ and $R^8$ independently selected from the group consisting of hydrogen, triarylsilyl, trialkylsilyl, t-butyl, diphenyl phosphine oxide, diphenyl phosphine sulfide, and combinations thereof.

26. The light emitting device of claim 15, wherein the emissive layer comprises a polymer comprising structural units of formula

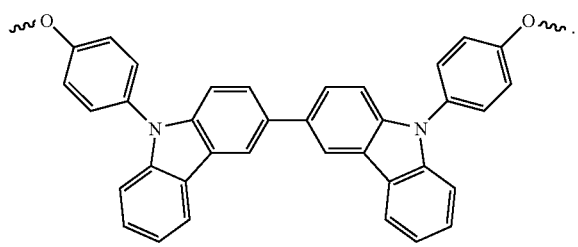
27. The light emitting device of claim 15, additionally comprising structural units of formula
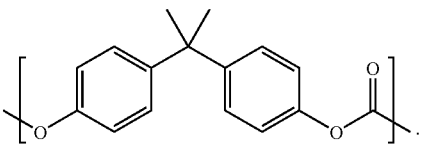
* * * * *